United States Patent [19]

Conway et al.

[11] Patent Number: 5,334,175
[45] Date of Patent: Aug. 2, 1994

[54] MALE URINARY INCONTINENCE DEVICE

[75] Inventors: Anthony J. Conway; Philip J. Conway, both of Chatfield; Richard D. Fryar, Jr., Rochester, all of Minn.

[73] Assignee: Rochester Medical Corporation, Stewartville, Minn.

[21] Appl. No.: 816,104

[22] Filed: Jan. 2, 1992

Related U.S. Application Data

[63] Continuation-in-part of Ser. No. 611,193, Nov. 9, 1990.

[51] Int. Cl.⁵ .......................... A61F 5/44; A61F 6/02
[52] U.S. Cl. .................................. 604/352; 128/844; 604/346; 604/347; 604/349
[58] Field of Search ................. 128/842, 844; 206/69; 604/346–347, 349–352, 355

[56] References Cited

U.S. PATENT DOCUMENTS

| | | |
|---|---|---|
| Re. 33,206 | 5/1990 | Conway et al. |
| D. 299,865 | 2/1989 | Kamstrup-Larsen et al. |
| 2,389,831 | 11/1945 | Welsh |
| 2,649,619 | 8/1953 | Killian |
| 3,403,682 | 10/1968 | McDonnell |
| 3,520,305 | 7/1970 | Davis ............................ 604/349 |
| 3,739,783 | 6/1973 | Broerman |
| 4,168,699 | 9/1979 | Hauser |
| 4,187,851 | 2/1980 | Hauser |
| 4,367,732 | 1/1983 | Poulsen et al. |
| 4,378,018 | 3/1983 | Alexander et al. |
| 4,475,910 | 10/1984 | Conway et al. |
| 4,477,325 | 10/1984 | Osburn |
| 4,534,768 | 8/1985 | Osburn et al. |
| 4,540,409 | 9/1985 | Nystrom et al. |
| 4,581,026 | 4/1986 | Schneider |
| 4,586,974 | 5/1986 | Nystrom et al. |
| 4,589,874 | 5/1986 | Riedel et al. |
| 4,626,250 | 12/1986 | Schneider |
| 4,640,688 | 2/1987 | Hauser |
| 4,699,616 | 10/1987 | Nowak et al. |
| 4,731,064 | 3/1988 | Heyden ......................... 604/352 |
| 4,759,753 | 7/1988 | Schneider et al. |
| 4,769,099 | 9/1988 | Therriault et al. |
| 4,820,289 | 4/1989 | Coury et al. |
| 4,846,909 | 7/1989 | Klug et al. |
| 4,863,449 | 9/1989 | Therriault et al. |
| 4,867,748 | 9/1989 | Samuelsen |
| 4,885,049 | 12/1989 | Johannesson |
| 4,894,059 | 1/1990 | Larsen et al. |
| 4,932,948 | 6/1990 | Kernes et al. |
| 4,963,137 | 10/1990 | Heyden ......................... 604/349 |
| 5,078,707 | 1/1992 | Klug ............................... 604/346 |
| 5,128,088 | 7/1992 | Shimomura et al. |

FOREIGN PATENT DOCUMENTS

| | | |
|---|---|---|
| 0390720 | 10/1990 | European Pat. Off. |
| WO86/00816 | 2/1986 | PCT Int'l Appl. |
| 2106784 | 4/1983 | United Kingdom |

Primary Examiner—David Isabella
Assistant Examiner—P. Zutarelli
Attorney, Agent, or Firm—Merchant, Gould, Smith, Edell, Welter & Schmidt

[57] ABSTRACT

A condom catheter having a sheath and a smaller diameter tube separated by a cone-shaped transition section with adhesive on the inner surface of the sheath and most of the transition section. The catheter is intended for a male having a recessed penis. The transition section is fastened to the penile tip such that the penile shaft may be pulled from pelvic skin so that the sheath can be unrolled onto the penile shaft so that when the penis recesses back into the pelvic skin, the catheter remains fastened to the penile shaft.

14 Claims, 5 Drawing Sheets

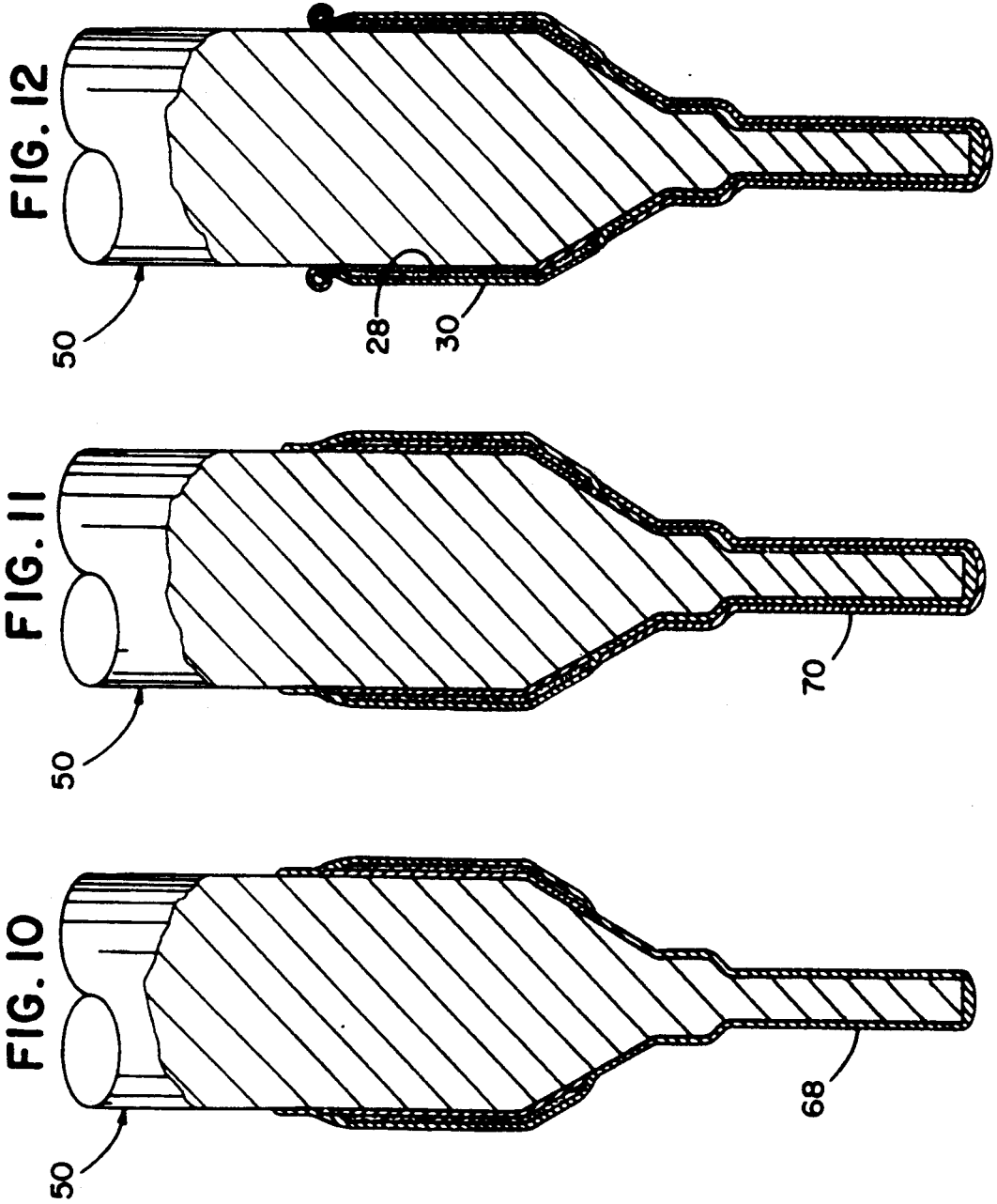

MALE URINARY INCONTINENCE DEVICE

CROSS-REFERENCE TO OTHER APPLICATIONS

The present application is a continuation-in-part application of co-pending U.S. patent application Ser. No. 07/611,193, filed Nov. 9, 1990, the disclosure of which is incorporated herein by reference.

FIELD OF THE INVENTION

The present invention relates to external urinary catheters or male condom catheters for channeling unrestrained urinary discharges into urine collection receptacles.

BACKGROUND OF THE INVENTION

Just a few years ago, external male urinary catheters, or condom catheters, were generally retained on a penis of an incontinent male with an adhesive tape of one type or another. The adhesive coated catheter disclosed by Conway et. al. (U.S. Pat. No. 4,475,910 reexamined and reissued as U.S. Pat. No. RE33,206) provided incontinent males with a self-sealing external catheter which required no tape, was easier to put on, and had functional advantages over earlier catheters, such as reduced leakage due to the improved seal between the catheter and the penis. The strapless catheter of Conway et. al. has proven to be a great commercial success and has become the catheter of choice for many men who are incontinent and who must wear an external urinary catheter.

Even the adhesive coated catheter of Conway et. al., however, is troublesome with respect to males having a "recessive" penis. A recessive penis is one wherein a relatively small length of penis protrudes from the pelvic area. In such situations, very often, less than one inch of penis presents itself for attachment of a catheter. Current "tape-on" and "strapless catheters," both of which were mentioned above, are extremely difficult to attach to males having a recessed penis. Often the only alternatives are diapers or the use of an internal catheter.

The strapless catheters on the market have the adhesive sandwiched between successive rolls of the catheter. As the catheter is unrolled, the inner surface comes into contact with the penile surface and is then "squeezed to seal." The adhesive on these catheters is positioned so that they will adhere to the penile shaft behind the glans. The glans is positioned within a non-adhering frontal section which is cone- or bulb-shaped. The recessive penis does not extend far enough out so that the strapless catheters can be unrolled far enough to bond sufficiently to the penile shaft. Because of the short length, it is also extremely difficult to tape a catheter securely to the recessive penis. The problem is well known and various solutions have been tried.

In one solution, a glans "cap" external catheter is shaped like a cup to fit only over the glans. It has been unsatisfactory, however, because a glans-only seal does not withstand body movement and urine pressure unless the adhesive is made so aggressive as to cause pain and damage on removal.

Other solutions have attempted to better install an ordinary strapless catheter on a recessed penis. One approach has been to partially unroll the strapless catheter and then position it over the recessed penis. This is a difficult installation procedure and results in another significant problem. Namely, as the strapless catheter is installed, it is common to pull out the recessed penis from its pelvic folds so as to be able to unroll enough of the strapless catheter to form a functional seal. Unfortunately, after installation, the penis retracts back into its pelvic recess and surrounding pelvic flesh actually push against the remaining unrolled roll on the catheter and essentially roll it back off the penis. To help prevent this, nurses have actually been instructed to try to cut off the remaining ring roll with a pair of scissors after the catheter is installed!

Another approach has been to use ostomy pouches to catheterize recessive penis patients. A flat circular adhesive material is sealed to the pelvic area around the penis and then the ostomy bag is adhered to that instead of the penis. Results are very unsatisfactory because the pelvic surface is difficult to adhere to and leakage is common. Ostomy hookups are also expensive.

The present invention overcomes the problems associated with installing an ordinary strapless catheter on a recessed penis.

SUMMARY OF THE INVENTION

The present invention is directed to a male urinary incontinence device for use on a penis with penile tip exposed and penile shaft recessed into pelvic skin. The device includes mechanism which has the ability to conform to the shape of the penile tip and to adhere to it. The mechanism includes a portion which can be unrolled onto and adhered to the penile shaft. The device further includes mechanism in fluid communication with the adhering and conforming mechanism, this second mechanism for pulling the penis from the pelvic skin in order to unroll the portion intended to adhere to the penile shaft. The pulling mechanism has an opening which can be placed in fluid communication with a urine receptacle.

More particularly, the device of the present invention includes a condom catheter having a sheath, a tube, and a transition section between the sheath and the tube. The sheath and the tube are each cylindrical. The sheath has a larger diameter than the tube. An adhesive coating adheres to the inner surface of a first portion of the sheath and to the inner surface of a second portion of the transition section. The two adhesive coated portions are contiguous. In this way, the transition section adheres to the penile tip or glans to hold it in order to pull the penile shaft from pelvic skin. The sheath then fastens to the penile shaft. The tube connects with a urine receptacle and can be used as a tool for pulling the penile shaft from pelvic skin after the transition section is fastened to the glans.

Importantly, the present device is structured so that a small protruding portion of the penis is used both as an area on which to seal the catheter and also an area which can, with the aid of the catheter device, be effectively used to pull out the penis from its recess in the fleshy part of the pelvis. Once it is pulled from its recessed position, the catheter device is sealed to the exposed penile shaft with no residual "ring roll" remaining. The penis can then withdraw back into the pelvis without pushing the catheter back off it. The new catheter device has a "short" sheath of only about 1.2 inches. The inside surface of the sheath is covered with adhesive except for about the last 0.1 inches at the open end. This provides for a short end ring to grasp to aid in removing the catheter device.

Unlike known catheters, with the present device the adhesive continues along the inner surface of the sheath from the adhesive-free ring down into the cone or transition section which necks down from the sheath to the tube. Also, unlike known catheters, the self-adhering cone area is thin-walled, similar to the sheath. During installation, the thin-walled cone area is simply "popped on" the small protruding tip of the recessive penis and is gently squeezed to seal it. As the catheter is gently pulled to extend the penis, the pelvic flesh can be pressed back and using the same hand that is pulling on the catheter, the sheath can be unrolled over the exposed penile shaft. This is easily done by pulling on the catheter with two middle fingers while unrolling the rest of the catheter with the index finger and thumb.

The present invention, therefore, solves the problems of known external condom catheters for use on recessive penises. To more clearly understand, however, this structure and these advantages of the present invention, attention is now directed to the drawings briefly described hereinafter and thereafter to the detailed disclosure which makes reference to the drawings.

BRIEF DESCRIPTION OF THE DRAWINGS

FIGS. 6-12 are a sequence which illustrate a method of making a condom catheter device in accordance with the present invention, FIG. 6 showing a blank mandrel in side view, FIG. 7 showing a cross-sectional view of the mandrel having been dipped in release agent, FIG. 8 showing a partial cross-sectional view having further been dipped in adhesive, FIG. 9 showing a cross-sectional view having been dipped in a solvent stripping agent, FIG. 10 showing a cross-sectional view having been dipped in silicone rubber, FIG. 11 showing a cross-sectional view having been dipped a subsequent time in silicon rubber to build the tube and lower cone region to a greater thickness, FIG. 12 showing in partial cross-sectional view a beginning roll of the sheath as a part of removing a condom catheter from the mandrel.

DETAILED DESCRIPTION OF THE PREFERRED EMBODIMENT

Figure 1:
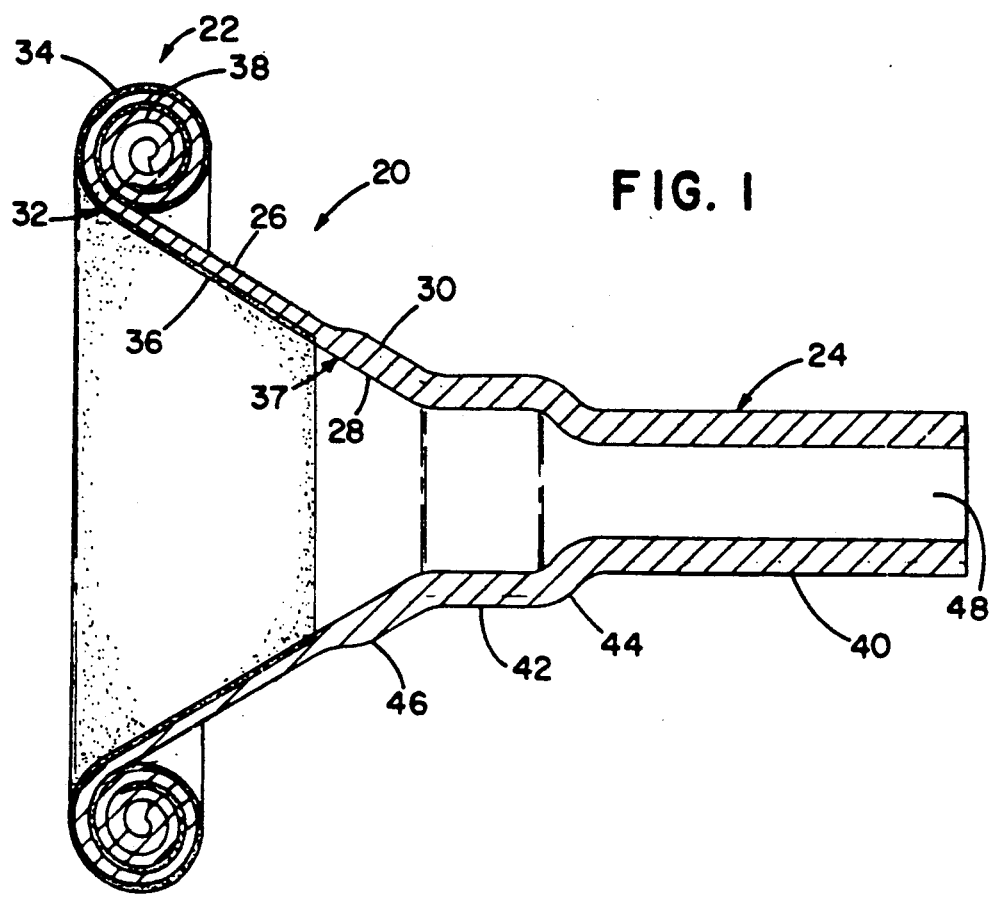
FIG. 1 is a cross-sectional view of a rolled-up condom catheter device in accordance with the present invention.

Referring now to the drawings wherein like reference numerals designate identical parts throughout the several views and referring more particularly to FIG. 1, a male urinary incontinence device or condom catheter device in accordance with the present invention is designated generally by the numeral 20.

Catheter device 20 has a unitary construction which includes a sheath 22, a tube 24, and a transition section 26 between the sheath 22 and tube 24. Catheter device 20 is made of silicone rubber. The silicone rubber has an inner surface 28 and an outer surface 30. Following manufacture and during pre-use storage, catheter device 20 has a pre-use configuration as shown in FIG. 1, wherein sheath 22 is a first portion 34 of rolled up on itself so that except as indicated hereinafter inner surface 28 is rolled up against and comes into contact with outer surface 30. Interposed between most of inner surface 28 and outer surface 30 of sheath 22 is an adhesive layer 32. Adhesive layer 32 adheres to inner surface 28 and does not adhere to outer surface 30 when sheath 22 is unrolled. The reason for such phenomenon is discussed in more detail hereinafter. Adhesive layer 32 also includes a second portion 36 formed on a significant portion of cone or transition section 26. First portion 34 and second portion 36 are contiguous as transition section 26 changes form to sheath 22.

Sheath 22 is formed as a cylinder having a diameter appropriate for a limp penis. Sheath 22 has a length of approximately 1.2 inches. Such length is long enough to provide sufficient fastening adhesion between first portion 34 of the adhesive layer 32 on the inside surface of the sheath and the penile shaft, but is not so long so that the sheath cannot be completely unrolled when a recessed penis is pulled outwardly to expose the total length of penile shaft with respect to pelvic skin. First portion 34 includes all of the inner surface of sheath 22 except an adhesive-free band 38 on the inner surface of sheath 22 adjacent its open end. Band 38 is intended to provide a loose end for a nurse to grasp and begin to roll sheath 22 back on itself or otherwise to remove an installed catheter device 20.

Cone or transition section 26 provides a reduction in diameter from sheath 22 to tube 24. Second portion 36 to which adhesive is applied contiguously with the adhesive on first portion 34 includes most of the cone portion of transition section 26. Since the idea is to provide sufficient adhesive surface within cone 26 to contact and adhere to the glans penis, it is important to provide a large adhesive surface for this purpose. However, an apex portion 37 which connects with and opens to tube 24 is preferably free of adhesive so that there is less chance that adhesive will seal together in front of the glans penis when the catheter 20 is attached thereto. Only sheath 22 is rolled in the pre-use configuration. Hence, second portion 36 on the inside surface 28 of transition section 26 is exposed (although the entire catheter device 20 is appropriately protected in a package of a type known to those skilled in this art). Sheath 22 and transition section 26 associated with the second portion thereof have a thickness which allows them to be conformed to the shape of the penis as the adhesive adheres to the penis. Tube 24 has a greater thickness so as to retain its shape and provide for suitable connection with additional tubing leading to a urine receptacle.

Tube 24 most efficiently provides a noncollapsing structure when formed in a smaller diameter section 40 and a larger diameter section 42. A short transitional neck 44 extends between sections 40 and 42. Likewise, the narrowest portion of the cone-shape of transition section 26 extends between larger diameter section 42 and the rest of transition section 26 so as to provide a short portion of greater thickness leading to the larger portion of transition section 26 having a thinner thickness. The distal end of tube 24 opens at opening 48 to provide for a urinary drainage tube junction designed to communicate through an appropriate drainage tube to a receptacle or collection device (not shown).

Although adhesive layer 32 adheres to the inner surface 28, it does not adhere to the outer surface 30 when sheath 22 is unrolled. Adhesive layer 32 is bonded to the inner surface 28 by a catalyzed process, preferably a vulcanizing process, in which constituents within the adhesive material are cross-linked to constituents within the silicone rubber which is formed from an unvulcanized silicone rubber solution overcoat layer during the vulcanizing process. Once the adhesive layer 32 is bonded to the inner surface 28 and the outer surface is formed according to the process discussed hereinafter, adhesive 32 no longer irreversibly adheres to outer surface 30. Although the adhesive will releasably adhere to outer surface 30, a moderate force separates the surfaces resulting in the adhesive remaining adhered to the inner surface 28. Contact between adhesive layer 32 and outer surface 30 is referred to as "releasable contact" or "releasable adherence." As indicated, this type of contact or adherence is characterized in that it permits a relatively easy separation of the adhesive from the particular surface.

Although, as described hereinafter, catheter device 20 can be made by combining two or more layers of a silicone rubber solution or of separate silicone rubber solutions, once the unvulcanized silicone rubber solutions are dried and cured in a vulcanizing process, the respective silicone rubber solution coatings are combined to form a single unitary wall without separate layers. In this regard, then, it is understood that any silicone rubber solution used to form silicone rubber products can be used to form the silicone rubber catheter device of the present invention. The vulcanizing process can be a heat process, a catalyzed process employing a catalyzing agent or agents, a combination of the two, or any other suitable vulcanizing process known in the art.

Figure 6:
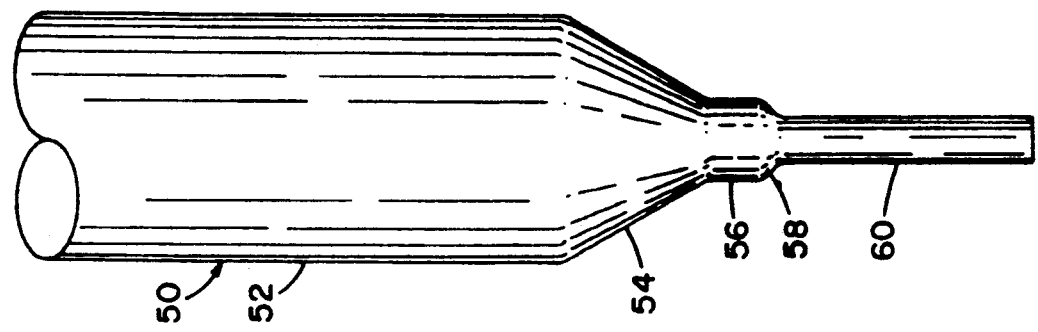

Referring now to FIGS. 6-12, the preferred method of making catheter device 20, described more fully in U.S. patent application Ser. No. 07/611,193 filed Nov. 9, 1990, herein incorporated by reference, includes a series of steps designed to coat mandrel 50. As shown in FIG. 6, mandrel 50 has a generally cylindrical shape which narrows from a large cylinder 52 along a major conical portion 54 to an intermediate cylindrical portion 6, from which it further narrows through a minor conical portion 58 to a narrow cylindrical portion 60. The surfaces of mandrel 50 are preferably coated with a material from which silicone rubber readily releases, such as a TEFLON (registered trademark of E. I. du Pont de Nemours and Company) material.

Figure 8:
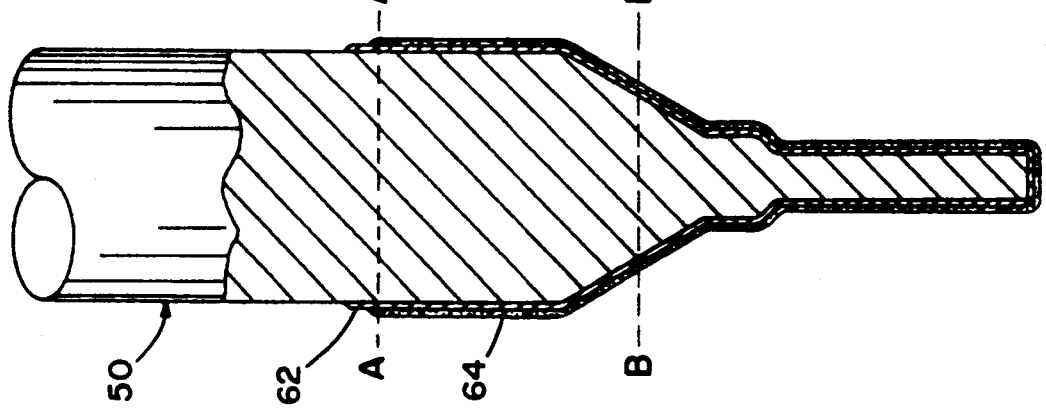
Figure 7:
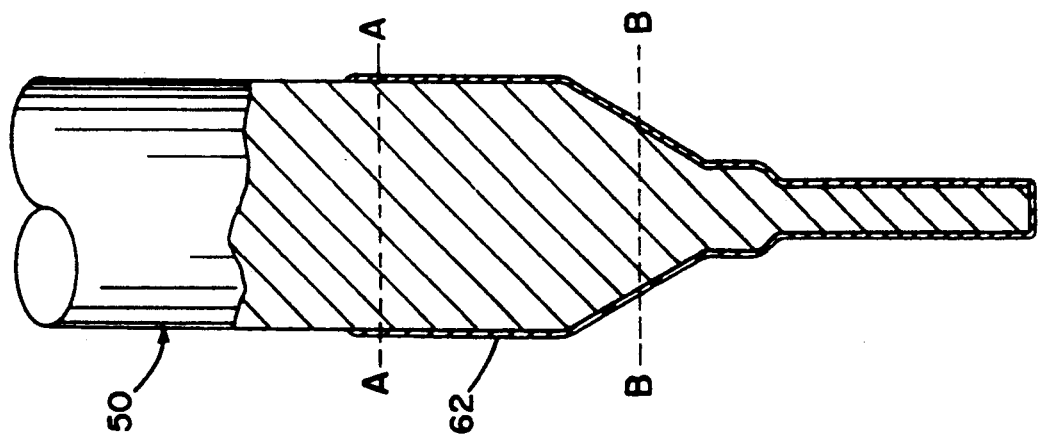

As indicated in FIG. 7, mandrel 50 is first dipped into a tank containing a release agent 62, preferably a polydimethylsiloxane fluid. A representative fluid which is appropriate is Dow Corning 360 medical fluid from Dow Corning, Inc., Midland, Mich. 48360 having a viscosity of 12,500 centistokes, diluted about 1:25, preferably about 1:100 in hexamethyldisiloxane. Release agent 62 is applied at least to line A. After the release agent is given time to dry, as illustrated in FIG. 8, mandrel 50 is next dipped in a tank of adhesive so that adhesive coats the mandrel at least up to line A, although not beyond the top edge of the release agent from the previous dipping. Although any adhesive material which will bond to unvulcanized silicone rubber during a vulcanizing process can be used, the preferred adhesive material in accordance with the present method is Monsanto 788 acrylic adhesive from Monsanto Corporation, St. Louis, Mo. Adhesive 64 is also then allowed to dry for a period of time.

Mandrel 50 is next dipped in a solvent, preferably trichloroethane (trichlor 1,1,1) or xylene, which will strip the adhesive coating 64 and the release agent coating 62 from the lower end 66 of mandrel 50. Mandrel 50 is dipped in the solvent only to line B so that the release agent 62 and the adhesive 64 fully coat mandrel 50 between lines A and B. In this regard, it is noted that line B is relatively close to intermediate cylinder 56 so that adhesive continues to cover a significant portion of the larger end of major conical portion 54.

After the cleaning step, as shown in FIG. 10, the mandrel is dipped in a tank containing a silicon rubber solution, preferably having a siloxane solvent, most preferably a hexamethyldisiloxane solvent. The disiloxane solvent is preferred because it does not destroy the integrity of the adhesive strip which remains on the portion of the mandrel between lines A and B following the stripping step. When the mandrel 50 is dipped into the silicon rubber solution, the unvulcanized solution coats the mandrel 50 and overcoats the release agent 62 and adhesive 64 to form a first overcoat layer 68 which extends beyond the top end of release agent 62. The unvulcanized silicone rubber overcoat layer 68 is then allowed to dry. Additional layers of silicone rubber solution can be added to obtain the desired thickness. In that regard, as shown in FIG. 11, it is important to the present invention that an additional layer of silicone rubber be applied to the lower portion of mandrel 50 to add greater thickness and structure to the tubular portion of catheter device 20 up to approximately where the adhesive remains. This additional thickness silicone rubber coating 70 is illustrated in FIG. 11.

Figure 13:
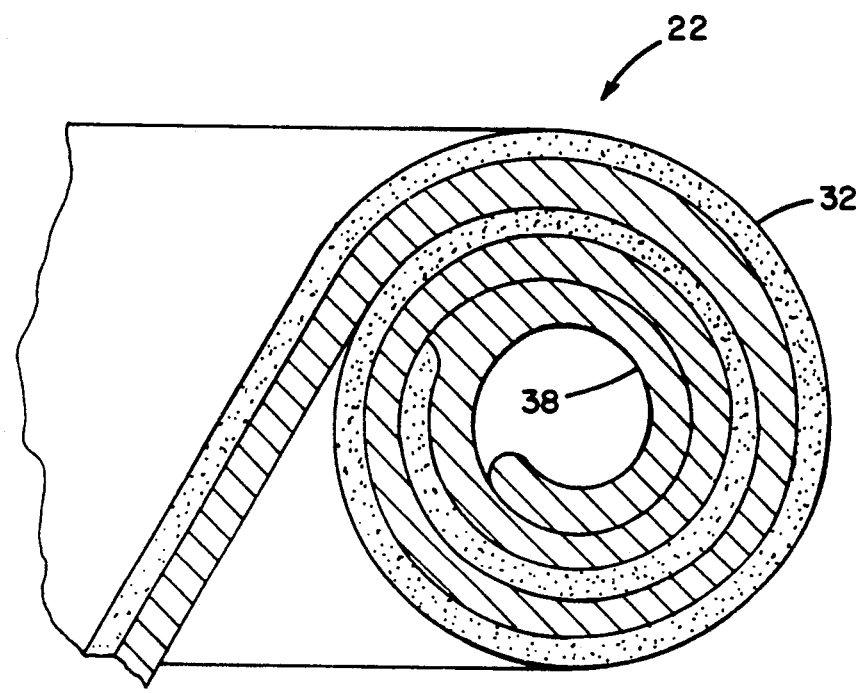
FIG. 13 shows an enlarged cross-sectional view of the sheath portion rolled up.

After layer 70 is allowed to dry and any additional layers applied to obtain desired thickness, the final silicone rubber overcoat layer along the entire length of catheter device 20 is vulcanized or cured at an elevated temperature, preferably about 205# F. It is understood and known by those skilled in the art to maintain the temperature at a level below the boiling point of the solvent or solvents used in the silicone rubber solutions which were used, so that the vulcanized silicone rubber which results will not have any bubbles caused by evaporation or boiling off of the solvent. It is further understood, of course, that other vulcanizing processes are equally applicable. In any case, during the vulcanizing process, any distinction between the initial silicone rubber solution and any subsequent layers are eliminated and a single unitary silicone rubber wall throughout device 20 is formed. Device 20 is allowed to cool and, as shown in FIG. 12, device 20 is then rolled from the top of mandrel 50 so that the inner surface 28 is rolled up onto outer surface 30. In the process of rolling, adhesive strip 64 which has now been integrally bonded with the silicone rubber during the vulcanizing process, comes into contact with the outer surface 30. An enlarged illustration of the sheath roll is illustrated in FIG. 13. When the sheath 22 is completely rolled, the conical portion and smaller tubular portions are pulled or otherwise removed from the mandrel and the end of the smallest tubular portion cut off to create opening 48. A portion of the release agent 62 may adhere to the adhesive. Any release agent which adheres, however, is absorbed eventually by the silicone rubber. This is important, since otherwise the release agent could interfere with the adherence of the adhesive to the penis during use of the catheter device 20. In this regard, it is noted that the adhesive is selected for its ability to bond with silicone rubber during the vulcanized process and for its lack of adherence when it comes into contact with vulcanized silicone rubber after the vulcanizing process. Furthermore, the adhesive must adhere sufficiently to the penis, while at the same time release from it without undue discomfort; particularly it must release from the glans portion of the penis without injury or undue discomfort. An appropriate adhesive was indicated earlier.

Figure 2:
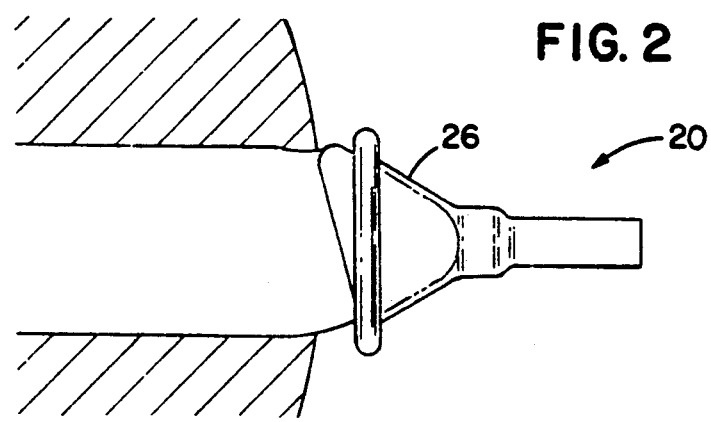
FIGS. 2-5 are a sequence showing use of the device, FIG. 2 showing in side view contact of the cone with the glans, FIG. 3 showing in side view pulling the penis with the catheter device to expose the penile shaft from pelvic skin, FIG. 4 showing in side view with a portion of the catheter cut away and adhesive remaining how the unrolled sheath fastens to the penile shaft, and FIG. 5 showing in side view with a portion of the sheath cut away how the penile shaft with sheath fastened thereto recesses back into pelvic skin.
Figure 3:
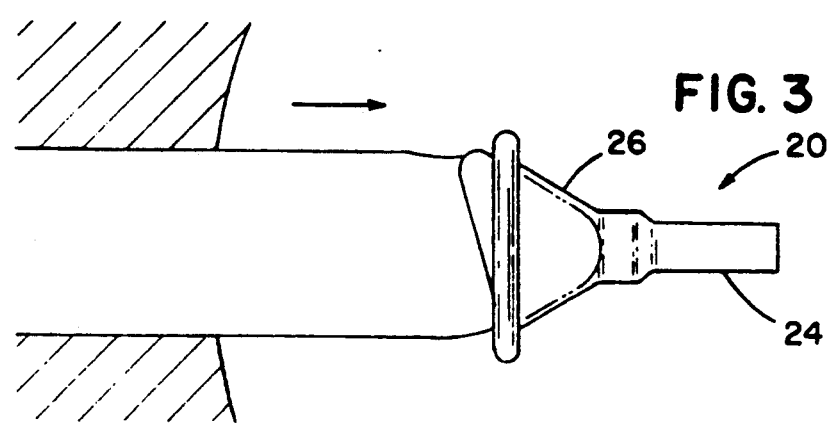
Figure 4:
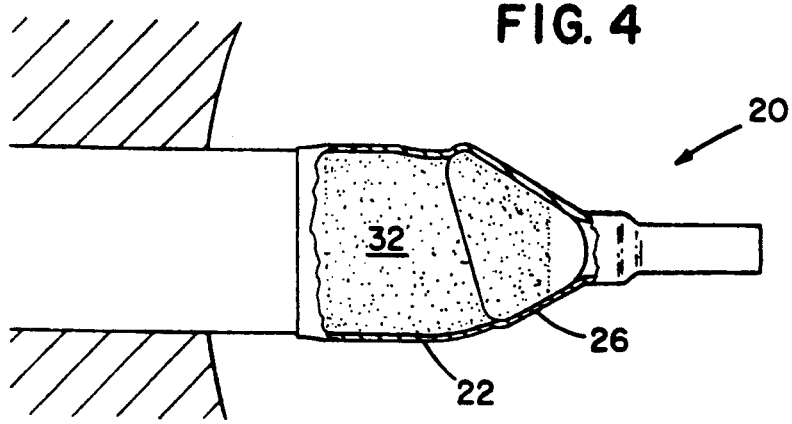
Figure 5:
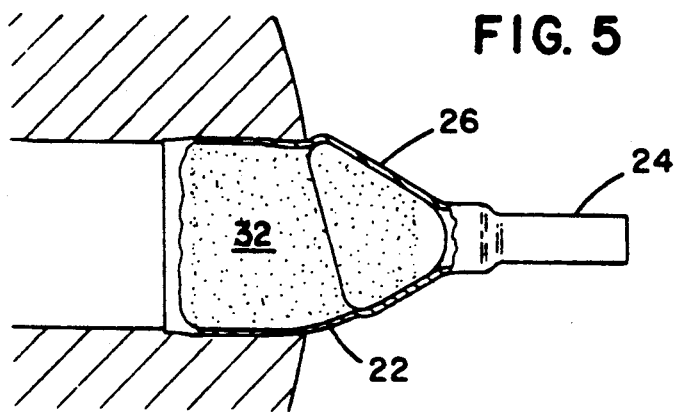
Figure 9:
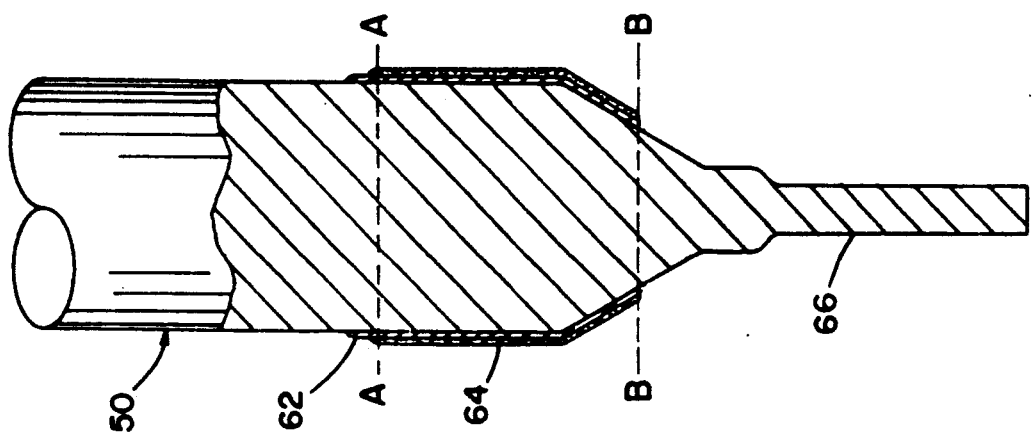

In use, catheter device 20 functions both as a tool to position a recessed penis for installation and then, of course, functions as a condom catheter to direct urine from an incontinent male to an appropriate receptacle. The various steps of application and use are illustrated in FIGS. 2-5. As indicated earlier, a recessive penis has minimal exposure of the penile shaft from the pelvic area and may only expose the glans. Such minimal exposure has made it difficult at least, and actually not even possible in many cases to fasten presently known condom catheters in a safe and functional fashion. With respect to device 20, as illustrated in FIG. 2, the transition section 26 is positioned next to and brought into contact with the glans. The most flexible portion of the transition section is gently pressed and pinched against the glans so that the adhesive adheres. The installer then pulls with tube 24 by holding tube 24 between the two middle fingers of one hand. As the penis extends, the other hand is used to hold back the pelvic flesh. The thumb and index finger of the hand holding device 20 are used to unroll sheath 22 onto the penile shaft. The sheath is pressed all around so that the adhesive adheres well and forms a good seal with the penis. The penis is extended sufficiently far from the pelvic skin so that the sheath can be completely unrolled as indicated in FIG. 4. Alternatively, the installer may find it easier to pull the catheter 20 by holding the transition section 26, in adherence to the glans, between the thumb and forefinger of one hand, and to unroll the sheath 22 with the thumb and forefinger of the other hand. Then, as indicated in FIG. 5, as the penis is allowed to recess back into the pelvic skin, the sheath remains adjacent to the penile shaft and does not roll up and come off the penis, but rather remains in a functional configuration. It is clear that device 20 should be positioned so that urine is directed directly into tube 24 from the attachment of transition section 26 to the penile tip. When removal is desired, tube 24 is again used as a tool to pull the recessed penis with one hand while holding the pelvic skin back with the other. The second hand, in holding back the skin, can then also readily lift and peel the adhesive-free band 38 of sheath 22 from the penile shaft and either pull the entire sheath back over itself or begin rolling it back over itself. In either case, the sheath is gently released from adherence with the penile shaft and similarly the transition section is gently pulled from the glans for complete removal.

Thus, although the present condom catheter device could be used with respect to any incontinent male, it is primarily intended for incontinent males having recessed penises. For that situation, device 20 solves the problems of known external urinary catheters. In this regard, however, although the present catheter device is directed toward a particular situation and the advantages and details of structure and function of the device have been set forth with respect to that situation, it is nevertheless understood that the disclosure herein, although presenting the preferred embodiment, is nevertheless exemplary. Consequently, any changes made, especially in matters of shape, size and arrangement to the full extent extended by the general meaning of the terms in which the appended claims are expressed, are understood to be within the principle of the invention.

What is claimed is:

1. A male urinary incontinence device, comprising:
   a condom catheter having a sheath, a tube, and a transition section between said sheath and said tube, said sheath and said tube being cylindrical, said sheath having a larger diameter than said tube, said condom catheter having an inner surface and an outer surface; and
   an adhesive coating on said inner surface on a portion of said sheath and a portion of said transition section, said portion of said sheath and said portion of said transition section being contiguous and for releasable adhesion to a wearer's male organ.

2. The device in accordance with claim 1 wherein said sheath and said transition section in a region of said portions have a thickness less than a thickness of said tube.

3. A self-adhesive condom-type male urinary catheter having interior and exterior surfaces, said self-adhesive condom-male male urinary catheter comprising a generally cylindrical sheath, a generally cylindrical tube and a generally conical transition section interconnecting the tube with the sheath such that a first interior space at least partially defined by the interior surface of the generally cylindrical sheath is in fluid communication with a second interior space at least partially defined by the interior surface of the generally cylindrical tube, said self-adhesive condom-type male urinary catheter further comprising a first adhesive coating on the interior surface of at least a portion of the generally cylindrical sheath and a second adhesive coating on the interior surface of at least a portion of the transition section and for releasable adhesion to a wearer's male organ.

4. The self-adhesive condom-type male urinary catheter of claim 3 wherein said first and second adhesive coatings are contiguous coatings on the interior surface of the catheter which form a continuous adhesive coating extending from an area on the generally cylindrical sheath to an area on the transition section.

5. The self-adhesive condom-type male urinary catheter of claim 3, said first and second interior spaces having first and second cross-sectional areas, respectively, wherein the first cross-sectional area is greater than the second cross-sectional area, and wherein the transition section has a first thickness extending between said interior and exterior surfaces, respectively, and said generally cylindrical tube has a second thickness extending between said interior and exterior surfaces, respectively, said second thickness being greater than said first thickness.

6. The self-adhesive condom-type male urinary catheter of claim 3 wherein the generally cylindrical sheath includes an adhesive-free band adjacent to the first adhesive coating.

7. The self-adhesive condom-type male urinary catheter of claim 3 wherein the generally cylindrical sheath is rolled up upon itself such that the interior surface is rolled up upon the exterior surface, wherein the first adhesive coating is at least partially rolled up upon the exterior surface of the generally cylindrical sheath.

8. The self-adhesive condom-type male urinary catheter of claim 7 wherein the first adhesive coating adheres to and is bonded to the interior surface of the generally cylindrical sheath, and wherein the first adhesive coating releasably adheres to the exterior surface of the generally cylindrical sheath when it comes into contact therewith such that the first adhesive coating can be separated from the exterior surface when the generally cylindrical sheath unrolled.

9. A self-adhesive condom-type male urinary catheter having interior and exterior surfaces, and self-adhesive condom-type male urinary catheter comprising a generally cylindrical sheath, a generally cylindrical tube and a generally conical transition section interconnecting the tube with the sheath such that a first interior space a least partially defined by the interior surface of the generally cylindrical sheath is in fluid communication with a second interior space at least partially defined by the interior surface of the generally cylindrical tube, said self-adhesive condom-type male urinary catheter further comprising a first adhesive coating on the interior surface of at least a portion of the generally cylindrical sheath and a second adhesive coating on the interior surface of at least a portion of the transition section, wherein said first and second adhesive coating are contiguous coatings on the interior surface of the catheter which form a continuous adhesive coating extending from an area on the generally cylindrical sheath to an area on the transition section for releasable adhesion to a wearer's male organ.

10. The self-adhesive condom-type male urinary catheter of claim 9, said first and second interior spaces having first and second cross-sectional areas, respectively, wherein the first cross-sectional area is greater than the second cross-sectional area, and wherein the transition section has a first thickness extending between said interior and exterior surfaces, respectively, and said generally cylindrical tube has a second thickness extending between said interior and exterior surfaces, respectively, said second thickness being greater than said first thickness.

11. The self-adhesive condom-type male urinary catheter of claim 9 wherein the generally cylindrical sheath is rolled up upon itself such that the interior surface is rolled up upon the exterior surface, wherein the first adhesive coating is at least partially rolled up upon the exterior surface of the generally cylindrical sheath.

12. The self-adhesive condom-type male urinary catheter of claim 11 wherein the first adhesive coating adheres to and is bonded to the interior surface of the generally cylindrical sheath, and wherein the first adhesive coating releasably adheres to the exterior surface of the generally cylindrical sheath such that the first adhesive coating can be separated from the exterior surface when the generally cylindrical sheath is unrolled.

13. The self-adhesive condom-type male urinary catheter of claim 12 wherein the generally cylindrical sheath includes an adhesive-free band adjacent to the first adhesive coating.

14. A self-adhesive condom-type male urinary catheter having interior and exterior surfaces adapted for use on a recessed penis, said self-adhesive condom-type male urinary catheter comprising:
- a generally cylindrical silicone rubber sheath, said generally cylindrical sheath having interior surface defining a first interior space, said first interior space having a first cross-sectional area;
- a generally cylindrical silicone rubber tube, said generally cylindrical tube having interior surface defining a second interior space having a second cross-sectional area smaller than said first cross-sectional area;
- a silicone rubber transition section interconnecting the tube with the sheath such that the first interior space defined by the interior surface of the generally cylindrical sheath is in fluid communication with the second interior space defined by the interior surface of the generally cylindrical tube;
- a first adhesive coating bonded to the interior surface of a portion of the generally cylindrical sheath; and
- a second adhesive coating bonded to the interior surface of a portion of the transition section, said second adhesive coating being contiguous with said first adhesive coating and for releasable adhesion to a wearer's male organ;
- wherein the generally cylindrical sheath is rolled up upon itself such that the interior surface is rolled up upon the exterior surface, wherein the first adhesion coating is at least partially rolled up upon the exterior surface of the generally cylindrical sheath such that the first adhesive coating releasably adheres to said exterior surface, and wherein said generally cylindrical sheath has an adhesive-free band adjacent to the first adhesive coating.

* * * * *